(12) United States Patent
Christensen et al.

(10) Patent No.: US 8,541,629 B2
(45) Date of Patent: Sep. 24, 2013

(54) HETEROCYCLIC AMINE CATALYST COMPOSITIONS FOR THE ALKOXYLATION OF ALCOHOLS TO GLYCOL ETHERS

(75) Inventors: Scott P. Christensen, Midland, MI (US); Derrick W. Flick, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 315 days.

(21) Appl. No.: 12/990,342

(22) PCT Filed: Apr. 17, 2009

(86) PCT No.: PCT/US2009/040934
§ 371 (c)(1),
(2), (4) Date: Oct. 29, 2010

(87) PCT Pub. No.: WO2009/134630
PCT Pub. Date: Nov. 5, 2009

(65) Prior Publication Data
US 2011/0054222 A1    Mar. 3, 2011

Related U.S. Application Data

(60) Provisional application No. 61/048,749, filed on Apr. 29, 2008.

(51) Int. Cl.
*C07C 41/03* (2006.01)
*C07C 43/13* (2006.01)
(52) U.S. Cl.
CPC ................. *C07C 41/03* (2013.01); *C07C 43/13* (2013.01)
USPC ............................ 568/678; 568/608; 568/618

(58) Field of Classification Search
CPC .......... C07C 41/03; C07C 43/13; C07C 43/11
USPC ................................................... 568/618, 678
See application file for complete search history.

(56) References Cited

U.S. PATENT DOCUMENTS

| 2,372,615 A * | 3/1945 | Hochwalt et al. ............. 568/662 |
| 3,560,574 A | 2/1971 | Frampton et al. |
| 3,910,878 A | 10/1975 | Mcada |
| 6,590,057 B1 * | 7/2003 | Brecht et al. .................... 528/52 |
| 2005/0004403 A1 | 1/2005 | Guttes et al. |

FOREIGN PATENT DOCUMENTS

| GB | 467228 | 6/1937 |
| JP | 5638323 | 4/1981 |
| JP | 7206744 | 8/1995 |
| JP | 200645258 | 2/2006 |

OTHER PUBLICATIONS

G.J. Stockburger, et al., The Journal of the America Oil Chemists' Society, vol. 40, No. 10, Oct. 1963, pp. 590-594.
Y. Arnould et al., Science Department of Nancy, Industrial Organic Chemistry, 1951, pp. 491-493.
O. Stephenseon, Journal of the Chemical Society, Chemical Society, Jan. 1, 1954, pp. 1571-1577.

* cited by examiner

*Primary Examiner* — Rosalynd Keys
(74) *Attorney, Agent, or Firm* — Whyte Hirschboeck Dudek S.C.

(57) ABSTRACT

Glycol ethers are made by a process in which an alcohol, an alkylene oxide and a catalytic amount of an aromatic, heterocyclic amine catalyst are contacted under reactive conditions. Representative catalysts include substituted and unsubstituted pyridines and imidazoles. The process uses known oxides and alcohols, and produces more mono- and di-adduct products than does a corresponding process using a caustic catalyst. Moreover, the process can be conducted at a lower reaction temperature than a corresponding process using a caustic catalyst without sacrificing oxide conversion rates yet producing fewer carbonyl impurities.

10 Claims, No Drawings

HETEROCYCLIC AMINE CATALYST COMPOSITIONS FOR THE ALKOXYLATION OF ALCOHOLS TO GLYCOL ETHERS

CROSS-REFERENCE TO RELATED APPLICATIONS

The present application claims priority to U.S. patent application Ser. No. 61/048,749, filed on Apr. 29, 2008, the entire content of which is incorporated by reference herein.

FIELD OF THE INVENTION

This invention relates to the production of glycol ethers. In one aspect, the invention relates to the production of glycol ethers by the alkoxylation of an alcohol while in another aspect, the invention is the production of glycol ethers by the alkoxylation of an alcohol using a heterocyclic amine catalyst.

BACKGROUND OF THE INVENTION

Caustic, e.g., sodium and/or potassium hydroxide, is the current commercial catalyst for the production of glycol ethers by the alkoxylation of an alcohol. These catalysts have been in use for over sixty years, and produce glycol ethers by way of a parallel-series reaction mechanism. The product mix from this process includes mono- and di-adducts (i.e., the lighter products) and tri-, tetra- and higher adducts (i.e., the heavier products). The market generally favors a product mix with a higher percentage of lighter products.

Moreover, in the production of glycol ethers from propylene oxide, both primary and secondary hydroxyl glycol ether product are made and because the former has toxicology issues associated with it, its presence in the final product mix is disfavored. The relative formation rate of the primary hydroxyl product increases with temperature which favors the use of low reaction temperatures, but caustic catalysts lose activity as the reaction temperature decreases. This, in turn, adversely affects the efficiency of the overall process.

Amines have been investigated as catalysts for the production of glycol ethers. These amine catalysts were primarily alkyl amines, e.g., triethyl amine, and these were found to be less active than caustic catalysts and produced larger amounts of impurities than the caustic catalyst system. In addition, these amine catalysts were found to quickly degrade by way of the Hofmann elimination reaction.

JP 2006/6045258 discloses the use of a tertiary amine having more than one active hydrogen as a catalyst in the manufacture of polyurethanes. JP 56-038323 discloses treating compounds having two or more active hydrogens with oxirane compositions in the presence of tetra-alkyl ammonium hydroxide to give polyalkylene glycol ether. Other patent disclosures of interest include GB 467228 (the production of glycol derivatives using a tertiary amine catalyst); FR 947250 (glycol derivatives using hexamethylenetetraamine); JP 1975/017976 (monoethoxylation of phenols using solvent and tertiary amines); JP 69-27570 (mono-glycol ethers of phenol produced by ethoxylation in the presence of a quaternary amine with a carboxylic acid); U.S. Pat. No. 3,560,574 (ethoxylation using trialkyl phosphines as catalysts); JP 1974/033183 (mono-glycol ethers of phenols prepared in the presence of trialkylbenzyl ammonium halides); and U.S. Pat. No. 3,910,878 (trialkylphosphonates and phosphines, phosphate esters as catalyst complexes with boron trifluoride). References that discuss the use of heterocyclic amines as catalysts include Ionescu, M., et al, *Imidazole, a High Efficiency Alkoxylation Catalyst*, Polyurethanes Conference 2000, pp. 311-322 (use of imidazoles as a catalyst for the alkoxylation reaction for the production of polyether polyols for polyurethane manufacture); Ricciardi, F., et al., *J. Mechanism of Imidazole Catalysis in the Curing of Epoxy Resin*, Poly, Sci.—Poly. Chem., Vol. 21, 1475-1490 (1983) (imidazoles and amines used as catalysts for epoxy curing); Hreczuch, W., et al., *Oxyethylation and Oxypropylation of Low Molecular Alcohols*, Ind. Eng. Chem, Res., 1999, 38, 2225-2230 (effect of triethylamine catalyst on the oxyethylation and oxypropylation of methanol, ethanol and butanol); Poskrobko, H., et al., *Oxyethylation and Oxypropylation of Low Relative Molecular Mass in the Presence of Amine-Type Catalysts*, J. Chem. Tech. And Biotech., 2000, 75, 547-552 (the effect of an amine catalyst on the oxyalkylation of alcohols); WO 2003/042281 (the manufacture of polyether alcohols by alkoxylation of H-functional precursors with amines, e.g., imidazoles, as catalysts); US 2005/0004403 (the production of polyether alcohols using amine, e.g., imidazoles, catalysts); and JP 72-06744 (the production of glycol ether using a tertiary amine catalyst, including pyridine, picoline and quinoline).

Accordingly, the glycol ether industry has a continuing interest in identifying catalysts that not only favor the production of a product mix with more light products and less heavy products, but also that works well at a reduced reaction temperature.

SUMMARY OF THE INVENTION

The invention is a process for is the production of glycol ethers by the alkoxylation of an alcohol using an aromatic, heterocyclic amine catalyst. In one embodiment, the invention is a process for producing glycol ether by contacting under reactive conditions an alcohol, an alkylene oxide and a catalytic amount of an aromatic, heterocyclic amine catalyst. Representative catalysts include substituted and unsubstituted pyridines and imidazoles. The process uses known oxides and alcohols, and produces more mono- and di-adduct products than does a corresponding process using a caustic catalyst. Moreover, the process can be conducted at a lower reaction temperature than a corresponding process using a caustic catalyst without sacrificing oxide conversion rates yet producing fewer carbonyl impurities.

DETAILED DESCRIPTION OF THE PREFERRED EMBODIMENT

All references to the Periodic Table of the Elements refer to the Periodic Table of the Elements, published and copyrighted by CRC Press, Inc., 2003. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application, or publication are incorporated by reference in their entirety (or its equivalent US version is so incorporated by reference) especially with respect to the disclosure of synthetic techniques, definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, monomer content, melt flow rate, etc., is from 100 to 1,000, it is intended that all individual values, such as 100, 101, 102, etc., and sub ranges, such as 100 to 144, 155 to 170, 197 to 200, etc., are expressly enumerated. For ranges containing values that are less than one or containing fractional numbers greater than one (e.g., 1.1, 1.5, etc.), one unit is considered to he 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, various process parameters.

The term "comprising" and its derivatives are not intended to exclude the presence of any additional component, step or procedure, whether or not the same is specifically disclosed. In order to avoid any doubt, all compositions claimed through use of the term "comprising" may include any additional additive, adjuvant, or compound whether polymeric or otherwise, unless stated to the contrary. In contrast, the tem, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination, As used with respect to a chemical compound, unless specifically indicated otherwise, the singular includes all isomeric forms and vice versa (for example, "hexane", includes all isomers of hexane individually or collectively). The terms "compound" and "complex" are used interchangeably to refer to organic-, inorganic- and organometal compounds. The term, "atom" refers to the smallest constituent of an element regardless of ionic state, that is, whether or not the same bears a charge or partial charge or is bonded to another atom. The term "heteroatom" refers to an atom other than carbon or hydrogen.

"Alcohol" includes, for the purpose of this disclosure, phenolic compounds.

"Glycol ether product" and similar terms means the reaction product produced by the reaction of an alcohol and an alkylene oxide under reaction conditions and with an aromatic, heterocyclic amine catalyst. For the purpose of this disclosure, glycol ether products comprise a light (or lighter) fraction and a heavy (or heavier) fraction. The light fraction comprises mono- and di-adducts, and the heavier fraction comprises tri-, tetra- and all larger adducts and any and all by-products, e.g., ethers other than the desired ether products, and carbonyl-containing species such as aldehydes and acetals. An "adduct" is one unit based on the alkylene oxide.

"Reaction conditions" and like terms generally refer to temperature, pressure, reactant concentrations, catalyst concentration, cocatalyst concentration, monomer conversion, product and by-product (or solids) content of the reaction mixture (or mass) and/or other conditions that influence the properties of the resulting product.

"Heterogeneous catalyst" and like terms means that the catalyst is in a different state of matter than the reactants, e.g., a solid, typically a finely-divided solid and/or supported on a carrier, while the reactants are liquid and/or gaseous, within the reaction mass under reaction conditions, In contrast, "homogeneous catalyst" means that the catalyst is in the same state of matter as the reactants, e.g., in solution with the reactants within the reaction mass and under reaction conditions.

"Reaction mass" and like terms means the mixture of reactants and catalyst, and optionally solvent, additives and the like, under reaction conditions in which the reactants are converted to products.

"Catalytically effective amount" and like terms means that sufficient catalyst is present in the reaction mass to increase the rate of reaction between the alcohol and the aliphatic or aromatic oxide over the rate of reaction in the absence of the catalyst.

The alkylene oxides (also known as epoxides) that can he used in the practice of this invention include ethylene oxide, propylene oxide, isobutylene oxide, 1,2-butylene oxide, 2,3-butylene oxide, and pentylene oxide; aromatic alkylene oxides such as styrene oxide; and cyclohexane oxide. These alkylene oxides may be used alone or in any combination with one another. Among the alkylene oxide compounds, preferred are aliphatic alkylene oxides having 2 to 4 carbon atoms such as ethylene oxide, propylene oxide, isobutylene oxide, and 2,3-butylene oxide. Although the alkylene oxide is typically added as a liquid, it can be added as a gas.

The alcohol (ROH) may, for example, be an aliphatic monohydric alcohol such as methanol, ethanol, propanol or n-butanol, an aliphatic dihydric alcohol such as ethylene glycol or propylene glycol, or a phenol such as phenol or methylphenol. Particularly preferred is a $C_{1-6}$ aliphatic monohydric alcohol, especially methanol, ethanol, propanol, butanol, pentanol and hexanol.

The alcohol component of this process can also be a phenol. Phenols, sometimes called phenolics, are a class of organic compounds consisting of a hydroxyl group (—OH) attached to an aromatic hydrocarbon group (Ar—). The simplest of the class is phenol (ArOH or $C_6H_5OH$). The phenolic compounds that can be used in the practice of this invention are typically monovalent and include phenol; phenols having a hydrocarbon substituent such as o-, m- or p-cresol, o-, m- or p-ethylphenol, o-, m- or p-t-butylphenol, o-, m-, or p-octylphenol, 2,3-xylenol, 2,6-xylenol, 3-5-xylenol, 2,4-di-t-butylphenol; phenols having a substituent group such as an aromatic substituent or an aromatic ring e.g., o-, m- or p-phenylphenol, p-(alpha-cumyl)phenol, and 4-phenoxyphenol; phenols having an aldehyde group such as o-, m- or p-hydroxybenzaldehyde; phenols having a substituent group with an ether linkage such as guaiacol and guaethol; phenols having a substituent group such as a hydroxyl group with a property inherent to alcohol (hereinafter, called as "alcoholic hydroxyl group") e.g., p-hydroxyphenethyl alcohol; phenols having a substituent group with an ester linkage such as p-hydroxy benzoic methyl, p-hydroxyphenylacetic acid methyl ester, and heptylparaben; and phenols having a halogen group such as 2,4,6-trichlorophenol. Among these, phenol and cresol are preferred. These phenols may be used alone or in any combination with one another.

The molar ratio of the alcohol and/or phenol to the alkylene oxide in the starting material is usually within a range of from 1:2 to 10:1, preferably from 3:1 to 7:1. The reactants, i.e., the alcohol and/or phenol and oxide, are preferably in the gaseous and/or liquid state.

The catalyst used in the practice of this invention is an aromatic, heterocyclic amine catalyst. Aromatic, heterocyclic compounds contain an aromatic ring structure that comprises carbon and at least one nitrogen atom. Aromatic, heterocyclic amine compounds also include condensed heterocycles such as indole. Representative aromatic, heterocyclic amine compounds include the pyrroles, pyrazoles, imidazoles, triazoles, benzimidazoles, pyridines, diazines, triazines, tetrazines, quinolines, phenanthrolines and indoles. The preferred catalysts are the pyridines and imidazoles. The catalyst can be added neat, or dissolved in a small amount of alcohol (typically the alcohol that is a reagent in the reaction), or formed in situ. The catalyst is used in a homogeneous manner, i.e., it is dispersed, preferably uniformly, through the reaction mass. Typically, the catalyst is mixed with the alcohol and/or phenolic compound before the alcohol and/or phenolic compound is mixed with the alkylene oxide. The catalyst is largely soluble in the alkylene oxide so as to render it homogeneous with the components of the reaction mass, but it can be bound to a solid support so as to render it heterogeneous within the reaction mass.

The catalysts used in the practice of this invention are used in a catalytically effective amount. Typically the minimum amount of catalyst used is at least 1, preferably at least 10 and more preferably at least 50, parts per million (ppm) based on the alcohol and/or phenol and alkylene oxide. The maximum amount of catalyst is typically limited only by considerations of economy and practical efficiency, and the typical maximum amount does not exceed 5,000, preferably it does not exceed 2,000 and more preferably it does not exceed 1,000, ppm based on the alcohol and/or phenol and alkylene oxide.

The reaction system may be a batch system, a semi-batch system or a continuous system. Whatever the system, however, sufficient contact between the reactants and catalyst is necessary to ensure efficient operation of the process. Accordingly, a suitable agitating means, e.g., propeller or other stirring mechanism, is typically employed in a batch system, and a suitable flow rate with turbulence is employed in a continuous system.

The minimum reaction temperature is typically at least 50, preferably at least 60 and more preferably at least 80, ° C. The maximum reaction temperature is typically not in excess of 250, preferably not in excess of 200 and more preferably not in excess of 180, ° C. The reaction pressure is usually from 1 to 50 kgf/cm$^2$ (0.098 to 4.9 MPa), preferably from 2 to 20 kgf/cm$^2$ (0.196 to 1.96 MPa).

The time required to complete a process according to the invention is dependent both upon the degree of alkoxylation desired (i.e., upon the average alkylene oxide adduct number of the product) as well as upon the rate of the alkoxylation reaction (which is, in turn, dependent upon temperature, catalyst quantity and nature of the reactants). One typical reaction time for the preferred embodiments of this invention is from 1 to 24 hours.

After the alkoxylation reaction has been completed, the product preferably is separated from the catalyst and cooled. The catalyst is separated and recovered from the remainder of the reaction mass by any conventional technique. If a liquid, then, for example, by distillation. If a solid, then, for example, by filtration or other liquid/solid separation technique. The catalyst can be recycled back to the reactor.

The use of an aromatic, heterocyclic amine as the catalyst for the production of glycol ether products, e.g., solvents, produces a lighter product mix, i.e., a higher selectivity to the desired mono- and di-alkoxylated products, than that produced by caustic catalysts under essentially the same reaction conditions using essentially the same reaction reagents. Typically, the selectivity ratio of lighter products (i.e., mono- and di-alkoxylated products) to heavier products (i.e., tri-, tetra- and higher adducts and by-products) is at least 2:1, more typically at least 20:1, still more typically at least 40:1, yet more typically at least 60:1 and even more typically at least 100:1. The incorporation of the nitrogen atom into the aromatic, heterocyclic structure significantly reduces or eliminates the degradation of the catalyst by way of the Hofmann degradation due to the conjugated nature of the cyclic structure as compared to the alkyl amines. In addition, during the production of glycol ethers from propylene oxide, the use of the aromatic, heterocyclic amine catalysts also allows for the reduction of the undesired primary hydroxyl glycol ether product without adversely affecting the production of the desired secondary hydroxyl glycol ether product.

The following examples illustrate certain specific embodiments of the invention. Unless otherwise indicated, all parts and percentages are by weight.

Specific Embodiments

Equipment and Procedure

The reactor is a 2-liter, stainless steel, batch reactor equipped with an agitator, an electric heater, an internal water-cooled cooling coil, a dip tube for sampling, an internal thermowell, various injection ports, and pressure relief venting. The reactor charge contains the desired amounts of alcohol and catalyst pressurized with nitrogen to 30-50 psig (0.207-0.345 mPa). The desired alkene oxide is administered to the system using a stainless steel addition cylinder suspended on a weigh cell. Cylinder nitrogen pressure is applied to the addition cylinder to aid in the transfer of oxide to the reactor. Pressure, temperature and weigh cell data are collected for each run with a stripchart recorder. The reaction temperature is maintained constant by the addition of cooling water in the cooling coils to offset the heat of reaction. Progress of the reaction is monitored by the pressure of the reactor. The reaction half-life is determined by measuring the time it takes for the pressure in the reactor to fall one-half of the total pressure drop achieved in the course of the reaction. Reactions are run until the pressure stabilizes; the reactor is then cooled to room temperature and drained. The reactions typically run for 120 to 180 minutes. Samples are taken immediately before oxide is added to the reactor and at the completion of the reaction. The samples are analyzed for composition by gas chromatography.

The alcohol/phenol, oxide and catalyst, and their respective amounts, and the reaction temperature and time, are reported in Table 1A. The half-life of the reaction and the final composition of the products and by-products are reported in Tables 1B, 1C and 1F.

TABLE 1A

Reagents and Amounts, and Reaction Temperature and Time

| Ex. # | ROH/ArOH | ROH/ArOH (g) | Catalyst | Cat (g) | Oxide | Oxide (g) | Rx Temp. (° C.) | Rx Time (min) |
|---|---|---|---|---|---|---|---|---|
| 1* | $C_4OH$ | 1001 | NaOH | 0.11 | EO | 128.2 | 160 | 90 |
| 2 | $C_4OH$ | 299.5 | TMP | 0.94 | EO | 42.8 | 160 | 150 |
| 3 | $C_4OH$ | 300.8 | IZ | 0.11 | EO | 40.3 | 160 | 150 |
| 4 | $C_4OH$ | 1001 | 2M-IZ | 0.41 | EO | 143.2 | 160 | 150 |
| 5* | $C_4OH$ | 1006.6 | NaOH | 0.11 | EO | 136.7 | 140 | 180 |
| 6* | $C_4OH$ | 998.2 | NaOH | 0.1 | EO | 139.4 | 120 | 300 |
| 7 | $C_4OH$ | 999 | 2M-IZ | 0.21 | EO | 135.5 | 160 | 240 |
| 8 | $C_4OH$ | 1002.1 | 2M-IZ | 0.21 | EO | 125.2 | 340 | 180 |
| 9 | $C_4OH$ | 999 | 2M-IZ | 0.2 | EO | 126.8 | 120 | 80 |
| 10 | $C_4OH$ | 998.7 | 2M-IZ | 0.21 | EO | 135.1 | 100 | 90 |
| 11 | ArOH | 282 | Pyridine | 0.124 | EO | 62.7 | 165 | 160 |
| 12 | ArOH | 281.4 | Pyridine | 0.257 | EO | 68.2 | 165 | 30 |
| 13 | ArOH | 284.5 | Pyridine | 0.51 | EO | 69.1 | 165 | 20 |
| 14* | MeOH | 202.7 | KOH | 0.17 | PO | 295.7 | 160 | 120 |
| 15* | MeOH | 197.6 | KOH | 2.61 | PO | 290.9 | 90 | 240 |
| 16* | MeOH | 197.2 | KOH | 3 | PO | 290.4 | 70 | 360 |
| 17 | MeOH | 201.6 | 1M-IZ | 0.9 | PO | 295.6 | 160 | 100 |
| 18 | MeOH | 200.7 | 1M-IZ | 0.21 | PO | 292.4 | 160 | 70 |
| 19 | MeOH | 207.7 | 1M-IZ | 0.92 | PO | 292.5 | 100 | 60 |
| 20 | MeOH | 200.6 | 1M-IZ | 0.69 | PO | 291.7 | 100 | 120 |
| 21 | MeOH | 200.3 | 1M-IZ | 0.26 | PO | 294.6 | 100 | 180 |
| 22 | MeOH | 205.4 | 1M-IZ | 0.9 | PO | 291.5 | 80 | 300 |
| 23* | $C_4OH$ | 1002.1 | NaOH | 1.13 | EO | 182.7 | 90 | 120 |
| 24* | $C_4OH$ | 1000.1 | NaOH | 1.12 | EO | 170.9 | 120 | 45 |
| 25* | $C_4OH$ | 997.6 | TEA | 2.98 | EO | 178.1 | 90 | 30 |
| 26* | $C_4OH$ | 1008.7 | TEA | 3.01 | EO | 185 | 120 | 60 |
| 27 | $C_4OH$ | 1000.7 | 2M-IZ | 2.43 | EO | 180.5 | 90 | 60 |
| 28 | $C_4OH$ | 1005 | 2M-IZ | 2.43 | EO | 176.7 | 120 | 15 |
| 29 | $C_4OH$ | 1000 | IZ | 1.99 | EO | 178.2 | 90 | 45 |
| 30 | $C_4OH$ | 1000.5 | IZ | 2.05 | EO | 186.5 | 120 | 20 |

*Comparative Example
ROH—Alcohol
ArOH—Phenol
$C_4OH$—n-Butanol
MeOH—Methanol
NaOH—Sodium Hydroxide
KOH—Potassium Hydroxide
IZ—Imidazole
1M-IZ—1-Methylimidazole
2M-IZ—2-Methylimidazole
TEA—Triethylamine
TMP—2,4,6-Trimethylpyridine
EO—Ethylene Oxide
PO—Propylene Oxide
Rx Temp—Reaction Temperature
Rx Time—Reaction Time The reaction half-life and the composition of the product mix of Examples 1-4 are reported in Table 1B. Examples 2-4 show the increased selectivity toward mono- and di-adducts obtained with catalysts of the present invention over that obtained with sodium hydroxide (Comparative Example 1) for butanol ethoxylation. The percentage of products which are tri-adduct and higher decreases from 12% with sodium hydroxide to less than 5% with a heterocyclic amine catalyst, and the lighter to heavier product ratio increases from under 7 to over 20. The improved selectivity is obtained at catalyst concentrations that give approximately equivalent activity as sodium hydroxide (as measured by oxide half-life) and equivalent generation of by-products as sodium hydroxide (as measured by the composition of total by-products in the final reaction mixture). The mono- and di-adducts are typically the most desired commercial products.

TABLE 1B

Examples 1-4 Reaction Half-Life and Composition of the Products

| Ex. # | Rx Half-Life (min) | Non-Glycol By-Products/Products (%) | Mono-Product (wt %) | Di-Adduct (wt %) | Tri- and Higher Adducts (wt %) | Light to Heavy Product Ratio |
|---|---|---|---|---|---|---|
| 1* | 19 | 1.32 | 66.42 | 20.69 | 12.90 | 6.75 |
| 2 | 33 | 0.75 | 78.66 | 18.23 | 3.11 | 31.15 |
| 3 | 13 | 0.62 | 74.75 | 20.93 | 4.32 | 22.15 |
| 4 | 25 | 0.92 | 75.49 | 19.87 | 4.64 | 20.55 |

*Comparative Example
Rx Half-Life—Reaction Half Life
By-Products—Non-alkylene oxide glycol ethers, e.g., mono- and di-butylene glycol, based on the combined weight of the by-products, the mono-product and the di- and higher adducts.
Mono-Product—Ethylene glycol butyl ether based on the combined weight of the mono-product and the di- and higher adducts.

TABLE 1B-continued

Examples 1-4 Reaction Half-Life and Composition of the Products

| Ex. # | Rx Half-Life (min) | Non-Glycol By-Products/ Products (%) | Mono-Product (wt %) | Di-Adduct (wt %) | Tri- and Higher Adducts (wt %) | Light to Heavy Product Ratio |
|---|---|---|---|---|---|---|

Di-Adduct—Diethylene glycol butyl ether based on the combined weight of the mono-product and the di- and higher adducts.
Tri- and Higher Adducts—Triethylene glycol butyl ether and higher adducts, e.g., tetra- and penta-, based on the combined weight of the mono-product and the di- and higher adducts.
Light to Heavy Product Ratio calculated by adding the weight percent of the mono- and di-products and dividing the sum by the weight percent of the tri- and higher adducts.

The reaction half-life and the composition of the product mix of Examples 1 and 5-10 are reported in Table 1C. Examples 7-10 show the increased catalytic activity of the present invention at lower temperatures over that obtained with sodium hydroxide (Comparative Examples 1 and 5-6) for butanol ethoxylation. The molar composition of the catalyst is approximately equal in Examples 1, and 5-10. The catalytic activity of the 2-methylimidazole is seen to increase as the temperature is lowered from 160° C. to 120° C. (as measured by oxide half-life), while the catalytic activity of sodium hydroxide decreases dramatically over the same temperature range. The catalytic activity of the 2-methylimidazole and sodium hydroxide are approximately equivalent at 140° C. at the given molar composition.

The comparison of Examples 6 and 9 shows that at 120° C. and at the same molar composition, the 2-methylimidazole demonstrates significantly higher catalytic activity (oxide half-life of 11 min) than sodium hydroxide (oxide half-life of 77 min). The comparison of Examples 6 and 10 shows that at the same molar composition, the 2-methylimidazole at 100° C. demonstrates higher catalytic activity (oxide half-life of 23 min) than sodium hydroxide at 120° C. (oxide half-life of 77 min) The better catalyst activity obtained with 2-methylimidazole compared to sodium hydroxide at temperatures below 140° C. allows production of glycol ethers at temperatures lower than are currently practically feasible, providing a reduction in impurities (particularly carbonyl impurities) formed at higher rates at increased temperature.

TABLE 1C

Examples 1-4 Reaction Half-Life and Composition of the Products

| Ex. # | Rx Half-Life (min) | Non-Glycol By-Products/ Products (%) | Mono-Product (wt %) | Di-Adduct (wt %) | Tri- and Higher Adducts (wt %) | Light to Heavy Product Ratio |
|---|---|---|---|---|---|---|
| 1* | 19 | 1.32 | 66.42 | 20.69 | 12.90 | 6.75 |
| 5* | 27 | 1.00 | 66.24 | 21.10 | 12.66 | 6.90 |
| 6* | 77 | 1.71 | 66.21 | 21.68 | 12.11 | 7.26 |
| 7 | 38 | 0.86 | 77.63 | 18.47 | 3.90 | 24.64 |
| 8 | 25 | 0.92 | 77.22 | 18.87 | 3.91 | 24.58 |
| 9 | 11 | 1.01 | 74.91 | 20.52 | 4.56 | 20.93 |
| 10 | 23 | 0.84 | 72.16 | 22.36 | 5.48 | 17.25 |

*Comparative Example
Rx Half-Life—Reaction Half Life
By-Products—Non-alkylene oxide glycol ethers, e.g., mono- and di-butylene glycol, based on the combined weight of the by-products, the mono-product and the di- and higher adducts.
Mono-Product—Ethylene glycol butyl ether based on the combined weight of the mono-product and the di- and higher adducts.
Di-Adduct—Diethylene glycol butyl ether based on the combined weight of the mono-product and the di- and higher adducts.
Tri- and Higher Adducts—Triethylene glycol butyl ether and higher adducts, e.g., tetra- and penta-, based on the combined weight of the mono-product and the di- and higher adducts.
Light to Heavy Product Ratio calculated by adding the weight percent of the mono- and di-products and dividing the sum by the weight percent of the tri- and higher adducts.

Examples 11-13 demonstrate the effectiveness of pyridine, a catalyst of the present invention, for the alkoxylation of phenol. Table 1D shows that the mono-adduct/di-adduct ratio can be varied from 8.6 to 26.1 with changes in the catalyst concentration at constant temperature and oxide concentration.

TABLE 1D

Mono- to Di-Adduct Ratio of Examples 11-13

| Ex. # | Mono-Adduct/ Di-Adduct Ratio* |
|---|---|
| 11 | 8.6 |
| 12 | 14.6 |
| 13 | 26.1 |

*Ethylene glycol phenyl ether to diethylene glycol phenyl ether.

Table 1E reports the results of Examples 14-22. Examples 17 and 18 show the increased selectivity toward mono-adducts obtained with a catalyst of the present invention (1-methylimidazole) over that obtained with potassium hydroxide (Example 14) for methanol oxypropylation. The mono-adduct/di-adduct ratio is 5.8-6.0 for these examples at 160° C. compared to 5.0 for potassium hydroxide. The mono-adduct is typically the most desired commercial product.

Examples 19-22 show the increased catalytic activity of 1-methylimidazole at lower temperatures over that obtained with potassium hydroxide (Examples 15 and 16) for methanol oxypropylation. Reaction times of between 60 and 300 minutes are obtained at temperatures of 80° C. and 100° C. with compositions of the present invention of between 500 and 2000 ppm. To obtain equivalent reaction times with potassium hydroxide at 70° C. and 90° C., 5000 to 6000 ppm is required. The difference in required catalyst amounts at lower temperatures is even more striking when calculated on a molar basis as the molecular weight of 1-methylimidazole is nearly 1.5 times that of potassium hydroxide. For example, to obtain the molar equivalent of catalyst that is in a 5000 ppm solution of potassium hydroxide, one would need 7300 ppm of 1-methylimidazole. The better catalytic activity obtained with the present invention compared to potassium hydroxide at temperatures at or below 100° C. allows for production of glycol ethers at temperatures lower than are currently practically feasible, providing an increase in the 1-methoxyl-2-propanol (PM2) to 2-methoxyl-1-propanol (PM1) ratio.

TABLE 1E

Mono- and Di-Adduct and PM-2/PM-1 Ratios of Examples 14-22

| Ex. # | Mono-Adduct/ Di-Adduct Ratio* | PM-2/PM-1 Ratio |
|---|---|---|
| 14 | 5.0 | 16.3 |
| 15 | 6.2 | 22.7 |
| 16 | 7.0 | 26.0 |
| 17 | 6.0 | 14.6 |
| 18 | 5.8 | 15.1 |
| 19 | 7.0 | 19.9 |
| 20 | 7.1 | 19.9 |
| 21 | 7.0 | 19.8 |
| 22 | 7.7 | 22.7 |

*Propylene glycol methyl ether to dipropylene glycol methyl ether.

Table 1F reports the results of Examples 23-30. Examples 27-30 show the decreased level of impurities obtained with the present invention (2-methylimidazole or imidazole) over that obtained with an aliphatic amine (Examples 25 and 26) for butanol ethoxylation. The molar composition of catalyst is approximately equal in Examples 23-30. The level of impurities is measured as a percentage of non-glycol by-products in the total products. The glycols, e.g., ethylene glycol, diethylene glycol, etc., are not counted as impurities as they are known, relatively innocuous compounds whose inclusion in the amount of impurities can mask the influence of less-desirable impurities, e.g., ethers other than the desired glycol ether products, carbonyl-containing species such as aldehydes and acetals, etc. The impurity level given by the present invention is 0.14 and 0.70 percentage points higher than that given by sodium hydroxide at 90° C. and 0.31 and 0.92 higher than that given by sodium hydroxide at 120° C. The impurity level given by the aliphatic amine is 1.39 percentage points higher than that given by sodium hydroxide at 90° C. and 1.74 percentage points higher than that given by sodium hydroxide at 120° C. This improved performance on impurity level is obtained while maintaining a product distribution very similar to the aliphatic amine; all the amine catalysts show similar increased selectivity toward mono- and di-adducts over that obtained with sodium hydroxide (Examples 23 and 24) for butanol ethoxylation. The lower level of impurities obtained with the present invention compared to aliphatic amines will allow production of glycol ethers with lower levels of impurities that potentially cause color, odor, and stability issues.

TABLE 1F

Examples 23-30 Reaction Half-Life and Composition of the Products

| Ex. # | Half-Life (min) | Non-Glycol By-Products/ Products (%) | Mono-Products/ Products (%) | Di-Products/ Products (%) | Tri-Products+/ Products (%) | Light to Heavy Product Ratio |
|---|---|---|---|---|---|---|
| 23 | 30 | 0.56 | 62.54 | 23.24 | 14.21 | 6.04 |
| 24 | 8 | 0.62 | 59.64 | 23.16 | 17.20 | 4.81 |
| 25 | 8 | 1.95 | 65.01 | 26.26 | 8.73 | 10.45 |
| 26 | 6 | 2.36 | 68.32 | 24.31 | 7.37 | 12.57 |
| 27 | 13 | 1.26 | 65.36 | 25.99 | 8.66 | 10.55 |
| 28 | 2 | 1.54 | 67.30 | 24.82 | 7.88 | 11.69 |
| 29 | 11 | 0.70 | 65.57 | 25.99 | 8.44 | 10.85 |
| 30 | 1 | 0.93 | 66.22 | 25.35 | 8.43 | 10.86 |

Light to Heavy Product Ratio calculated by adding the weight percent of the mono- and di-products and dividing the sum by the weight percent of the tri- and higher adducts.

The present invention is not limited to the preceding embodiments, but includes modified forms of those embodiments including portions of the embodiments and combinations of elements of different embodiments as may come within the scope of the following claims.

What is claimed is:

1. A process of producing a glycol ether product, comprising the step of contacting
   (i) an alcohol selected from the group consisting of an aliphatic monohydric alcohol and a phenolic alcohol;
   (ii) at least one alkylene oxide selected from the group consisting of ethylene oxide and propylene oxide, and
   (iii) a catalyst amount of at least one aromatic, heterocyclic amine selected from the group consisting of imidazole, benzimidazole, 1-methylimidazole, and 2-methylimidazole;
   at a temperature between 50 and 160° C. and a pressure between 0.098 and 4.9 MPa, the alcohol and the alkylene oxide present at a molar ratio within a range of from 1:2 to 7:1, and the aromatic, heterocyclic amine present in an amount between 1 and 5,000 ppm based on the combined amount of alcohol and alkylene oxide.

2. The process of claim 1, wherein the glycol ether product comprises a light fraction comprising mono- and di-adducts and a heavy fraction comprising tri- and greater adducts and all by-products, and the temperature, the molar ratio of the alcohol and the alkylene oxide, and the amount of the aromatic, heterocyclic amine are effective to produce the glycol ether product at a lighter fraction to heavier fraction selectivity ratio of at least 2:1.

3. The process of claim 2, wherein the glycol ether product is produced at a lighter fraction to heavier fraction selectivity ratio of at least 20:1.

4. The process of claim 2, wherein the glycol ether product is produced at a lighter fraction to heavier fraction selectivity ratio of at least 40:1.

5. The process of claim 1, wherein the aromatic heterocyclic amine is imidazole, benzimidazole or 2-methylimidazole.

6. The process of claim 1, wherein the alcohol is a $C_{1-6}$ aliphatic monohydric alcohol.

7. The process of claim 1, wherein the alcohol is phenolic alcohol.

8. The process of claim 1, wherein the aromatic heterocyclic amine is present in an amount between 50 and 1,000 ppm based on the combined amount of alcohol and alkylene oxide.

9. The process of claim 1 in which the alcohol, an alkylene oxide and heterocyclic amine are contacted at a pressure between 0.196 and 1.96 MPa.

10. The process of claim 1 in which the alcohol, the aklylene oxide and aromatic, heterocyclic amine catalyst are contacted at a temperature between 50 and 120° C.

* * * * *